United States Patent [19]

Stover et al.

[11] 4,321,465
[45] Mar. 23, 1982

[54] INFRARED ASSAY OF KEROGEN IN OIL SHALE

[75] Inventors: Carole S. Stover, Irvine; Leslie E. Compton, Claremont, both of Calif.

[73] Assignee: Occidental Research Corporation, Irvine, Calif.

[21] Appl. No.: 196,773

[22] Filed: Oct. 14, 1980

Related U.S. Application Data

[63] Continuation of Ser. No. 40,979, May 21, 1979, abandoned.

[51] Int. Cl.³ .......................... G01V 5/00; G01J 1/00; G01D 18/00
[52] U.S. Cl. ................................... 250/255; 250/301; 250/341; 250/252
[58] Field of Search ............... 250/255, 253, 340, 341, 250/252, 339, 301; 356/70, 73

[56] References Cited

U.S. PATENT DOCUMENTS

| | | | |
|---|---|---|---|
| 2,500,213 | 3/1950 | Stevens | 250/255 |
| 3,496,350 | 2/1970 | Bray | 250/255 |
| 3,631,246 | 12/1971 | Defriez | 250/341 |
| 3,762,817 | 10/1973 | Harklov | 356/73 |
| 4,149,804 | 4/1979 | Chew | 356/416 |
| 4,149,805 | 4/1979 | Chew | 356/416 |

OTHER PUBLICATIONS

Shaks, et al., "Infrared Spectra of Organic Minerals", Tr. Vses. Neft. Nauchno-Issled. Geologorazved. Inst., 1974, pp. 329, 131 (Chem. Abs., vol. 84, 76638u, 1976).
Robin, et al., "Contribution of Molecular Water in the Infrared Spectra of Kerogens and Coals", Fuel, 1976, 55(3), pp. 177-183 (Chem. Abs., vol. 85, 110688t, 1976).
Espitalie, et al., "Étude de la Matiere Organique Insoluble (Kérogène) des Argiles du Toarcim du Bassin de Paris", Revue de L'Institut Francais du Pétrole, vol. 28, No. 1, Jan. 1973, pp. 37-66.

*Primary Examiner*—Alfred E. Smith
*Assistant Examiner*—Carolyn E. Fields
*Attorney, Agent, or Firm*—Christie, Parker & Hale

[57] ABSTRACT

A method for determining kerogen content in oil shale is disclosed. The kerogen content of oil shale is measured by transmitting light of the infrared region of the electromagnetic spectrum through a sample containing comminuted oil shale and determining the amount of light absorbed by the kerogen in such sample. The amount of light of a selected wave number absorbed by the sample of comminuted oil shale is proportional to the Fischer Assay determination of kerogen content of such a sample. An internal standard having an absorbance within the infrared region of the electromagnetic spectrum at a wave number other than wherein oil shale has an absorbance is integrated into the sample of oil shale for providing an indication of the kerogen content within the oil shale sample upon comparison of the relative absorbance at the respective wave number of selected infrared light for the internal standard and the kerogen.

16 Claims, 1 Drawing Figure

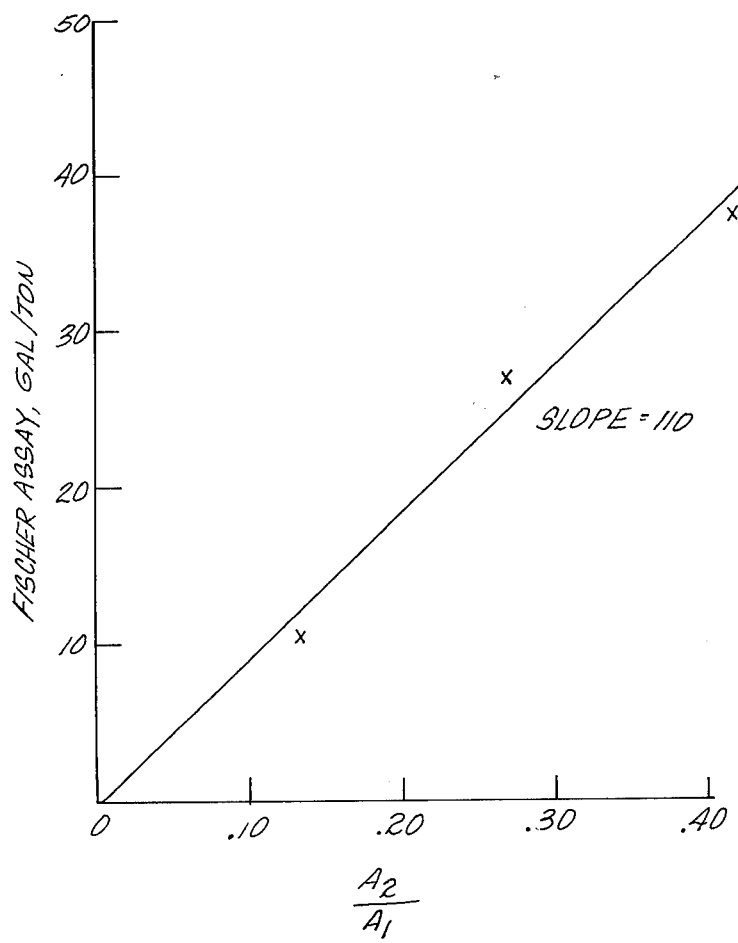

INFRARED ASSAY OF KEROGEN IN OIL SHALE

CROSS REFERENCE TO RELATED APPLICATIONS

This is a continuation of application Ser. No. 040,979, filed May 21, 1979, now abandoned.

BACKGROUND OF THE INVENTION

This invention relates to a method for determining the kerogen content of oil shale. The kerogen analysis of this invention can be performed immediately without requiring laboratory analysis and complex calculations, or destructive techniques.

Vast untapped reserves of shale oil in the form of oil shale exist in this country as well as other locations throughout the world. Increased attention is being devoted to the exploitation of oil shale because of the current need for new energy sources.

The term "oil shale" as used in industry is, in fact, a misnomer, because it is neither shale, nor does it contain oil. It is a sedimentary formation comprising marlstone deposits interspersed with layers containing an organic polymer called "kerogen" which upon heating decomposes to produce carbonaceous liquid and gaseous products. It is the formation containing kerogen that is called "oil shale" herein, and the carbonaceous liquid product is called "shale oil."

Oil shale deposits occur in generally horizontal beds, and within a given bed there are an extremely large number of generally horizontal deposition layers containing kerogen known as "varves." The varves typically are nonuniformly dispersed throughout a given bed. In the higher grade oil shales, the varves are commonly cemented together into relatively thick, compact layers. The lower grade oil shales have much thinner varves spaced apart through the bed. For example, a core sample taken from a typical bed may vary from thick, solid oil shale sections to layered sections having the appearance of poker chips. In the core, small layers or nodules of other minerals and rock materials are sometimes found interspersed between the varves containing kerogen. Typical of these other minerals are nahcolite, dawsonite, other salines, dolomite, mudstone, sandstone, tuffs, analcite and bentonite.

Techniques for preparing oil shale for retorting generally comprise explosively expanding a subterranean oil shale formation to form a fragmented, permeable mass of particles containing oil shale. Shale oil then may be recovered from the particles by in situ retorting techniques, or by retorting in surface retorts, for example.

Prior to preparing the oil shale for retorting, the formation is explored to determine the location within the formation containing the highest grades of oil shale. Core samples are taken from the formation and subjected to laboratory analysis to determine the kerogen content of the sample. One such analytical technique is the "Fischer assay" in which a sample customarily weighing 100 grams and representing one foot of core is subjected to controlled laboratory analysis involving grinding the sample into small particles which are placed in a sealed vessel and subjected to heat at a known rate of temperature rise to measure the kerogen content of the core sample. Kerogen content is usually stated in units of "gallons per ton," referring to the number of gallons of shale oil recoverable from a ton of oil shale heated in the same manner as the Fischer analysis.

Such analytical techniques are generally done in laboratories far from the drilling site. This causes a considerable delay before analytical results are available to field personnel conducting the exploration tests. Thus, immediate field decisions on the progress of the exploration program cannot be based on accurate analysis of core samples.

The present invention provides a method for rapidly determining the kerogen content of oil shale. The invention does not require complex calculations or destructive laboratory techniques characteristic of the Fischer assay and other known methods for measuring kerogen content. The invention uses a very small sample which makes it possible to accurately analyze a core sample of oil shale in the field and still have the core sample available for other purposes, such as for corroborating laboratory measurements to be conducted later at a more convenient time. The sample for analysis can be taken along the length of a core, leaving most of the core intact. Thus, field decisions on the progress of the exploration program can be made immediately, rather than waiting for several days, which is a common delay for kerogen assay by Fischer analysis.

SUMMARY OF THE INVENTION

According to a presently preferred embodiment of the invention, the kerogen content of oil shale is measured by transmitting light of a preselected wave number within the infrared region of the electromagnetic spectrum through a sample of comminuted oil shale and determining the amount of such infrared light absorbed by the kerogen in such a sample. The amount of light of the selected wave number absorbed by the sample of comminuted oil shale is proportional to the kerogen content of such a sample. An internal standard, having an absorbance within the infrared region of the electromagnetic spectrum at a wave number other than a band wherein oil shale has an absorbance, can be integrated into the sample of oil shale for providing an indication of the kerogen content within the oil shale sample upon comparison of the relative absorbance at the respective wave numbers for the internal standard and the kerogen.

BRIEF DESCRIPTION OF THE DRAWING

The drawing represents a graph of shale oil content by Fischer Assay plotted along the Y-axis and the ratio of absorbances of kerogen to internal standard plotted along the X-axis.

DETAILED DESCRIPTION OF THE INVENTION

This invention is based on a recognition that the kerogen content of oil shale is proportional to the amount of infrared light absorbed by the oil shale. A solid sample of oil shale can be immediately and nondestructively analyzed for kerogen content, according to a presently preferred embodiment of this invention, by transmitting infrared light of a selected wave number within an absorption band for kerogen in oil shale through a sample containing comminuted oil shale and detecting the amount of infrared light absorbed by the sample. Preferably, the amount of light of the selected wave number that is absorbed is determined by sensing the amount of light transmitted through the sample. The amount of light absorbed is calculated from the amount of light transmitted. The amount of light absorbed by the sample is proportional to the amount of kerogen within the sample.

The absorbance of light by a compound as measured by a spectrophotometer, can be expressed by the Beer-Lambert law:

$$A = EIC \qquad (1)$$

wherein A is the absorbance, E is the absorptivity of the light-absorbing substance at the chosen frequency (wave-number) or wavelength, I is the path length of light through the sample and C is the concentration of the absorbing substance in the sample. The path length of light through a sample is difficult to regulate and maintain constant for solid samples. Accordingly, an internal standard is added to the sample of oil shale to facilitate the kerogen concentration determination. An internal standard is selected from compounds having an absorbance at a band width within the infrared region of the electromagnetic spectrum different from the characteristic band widths of kerogen and oil shale. Such an internal standard can be a compound or mixture of compounds selected from the group consisting of KCN, KSCN, and KBr, with the proviso that KBr can not be used alone. KCN has a characteristic absorbance signal attributable to the C N bond at about 2100 cm$^{-1}$ which is within a band of the infrared region in which oil shale does not absorb.

The absorbance of such an internal standard at about 2100 cm$^{-1}$ can be given by the Beer-Lambert law and expressed by the formula:

$$A_1 = E_1 I_1 C_1 \qquad (2)$$

The corresponding absorbance of the kerogen in the sample at a wave number other than that for the internal standard can then be given by the Beer-Lambert Law and expressed by the formula:

$$A_2 = E_2 I_2 C_2 \qquad (3)$$

With careful preparation of the solid samples, the path lengths for the internal standard, $I_1$, and the path length for the kerogen, $I_2$, are substantially equal. The ratio of the absorbance for the internal standard of infrared light at its characteristic wave number band to the absorbance of infrared light by the kerogen at one of its characteristic wave number bands can thereby be represented by the formula:

$$(A_1/A_2) = (E_1 C_1 / E_2 C_2) \qquad (4)$$

The concentration of kerogen $C_2$ within the sample can then be derived and expressed as:

$$C_2 = C_1 \cdot (E_1 A_2 / E_2 A_1) \qquad (5)$$

The concentration $C_1$ of the internal standard and the absorptivity $E_1$ are both constants for all samples standardized with the same concentration of the internal standard and with a standardized background. The absorptivity $E_2$ for kerogen is assumed to be fairly constant for all grades of kerogen within a particular formation of oil shale. Therefore, the constant represented by the expression $(C_1 E_1 / E_2)$ can be determined by measuring the absorbances of the internal standard and kerogen and calculating the ratio $A_2/A_1$, for a sample for which the kerogen content is known. For example, a sample of oil shale upon which a Fischer assay has been conducted can be used in determining the value of the constant.

The constant defined by $(C_1 E_1 / E_2)$ can be expressed in any convenient units. The units can be selected to provide any desired manner of stating the kerogen concentration; such as, gallons per ton, grams per ton, liters per ton, liters per kilogram-ton and the like. As the absorbance of kerogen is proportional to the concentration of kerogen and provides a straight-line linear relationship, any such units of measurement of concentration can be used.

Once the constant has been determined, it is elementary mathematics to determine the concentration of kerogen within a sample of oil shale by measuring the relative absorbance of the oil shale and internal standard with infrared spectroscopy at their respective wavelength bands and substituting those values into the above equation (5) and solving for $C_2$.

In another manner, the ratio of the absorbances $A_2/A_1$ can be plotted on a graph against the concentration of kerogen within a sample of oil shale. When the absorbance ratios for known concentrations of kerogen within samples are plotted along the X-axis, a straight line curve is generated on a graph having a slope equal to the constant $(C_1 E_1 / E_2)$. Again, the concentration can be expressed in any convenient or desired units. Following the creation of such a graph, samples of oil shale, having unknown concentration of kerogen, can be subjected to infrared spectroscopy and the relative absorbances measured for the kerogen and internal standard. By determining on the graph the point of intersection of the plotted straight line curve and the line representative of the ratio of the absorbances, the concentration of kerogen within the oil shale is determined.

The infrared light referred to herein is light of the electromagnetic spectrum having a wavelength of from about 2.5 to about 16 microns which light has a wave number from about 4000 to about 625 cm$^{-1}$. The entire infrared region recited above is used to scan a sample of comminuted oil shale. The sample of comminuted oil shale is scanned to determine the characteristic absorption bands within the infrared region for the kerogen in the sample. From these characteristic absorption bands there is selected a particular band, or wave number of light, at which the absorbance is to be measured. The most suitable wave number for the quantitative measurements of the method of this invention is not necessarily the wave number at which the absorbance is greatest. For this reason, it is desirable to prepare the complete infrared absorption spectrum for an oil shale sample to determine the wave number to be used for measuring the absorbance, $A_2$, of all subsequent samples.

Generally, a wave number corresponding to an absorption peak is selected for use in measuring the absorbance as the greatest slope in the curve relating absorbance to concentration is obtained at an absorption peak; as a result, a maximum in sensitivity is realized at such a wave number.

The wave number for determining the amount of kerogen in oil shale is selected such that it is representative of the kerogen present, is not masked by other absorbing bands and is not subject to a wide variance in absorption due to the presence or non-presence of constituents in the oil shale which are unrelated to the kerogen concentration. It was found that the absorption peak characteristic of carbon-hydrogen aliphatic bond (C—H) stretching is the preferred wave number of infrared light having the above qualities for measurement of absorbance of kerogen and for quantitatively determining the kerogen content of an oil shale sample. Such a characteristic peak for the carbon-hydrogen bond in kerogen was found to be at about 2900 cm$^{-1}$, which is about 3.45 microns in wavelength.

The absorption peak for the oxygen-hydrogen (O—H) bond was not selected. The absorption band for the O—H bond is broad and ranges from 2.8 to 3.3 microns. Further, the O—H bond is sparingly present in low concentrations in kerogen. The O—H absorbance due to the O—H within the kerogen can be occulted by the O—H bonds present in any water which can be in the sample and/or present in some minerals that can also be found in the oil shale.

The absorption peak for nitrogen-hydrogen (N—H) bonds was also not selected as such a peak is relatively broad and such bonds are only present in low concentrations in kerogen. Further, the N—H bonds attributable to the kerogen present in the sample of oil shale can be occulted by minerals within the oil shale.

The absorption peak for the sulfur-hydrogen (S—H) bond at about 3.82 microns (2550 cm$^{-1}$) was not selected due to the lack of correlation between sulfur and kerogen. the absorption attributable to the S—H bonds was found not to directly relate to the kerogen content within a given sample when compared to the Fischer assay for that sample.

An absorption peak was found on the infrared spectrogram for oil shale at about 5.5 microns ($\sim$1850 cm$^{-1}$) which represented the carbon to oxygen double bond (C=O). This peak was not selected since only low concentrations of C=O are present in kerogen. The C=O absorption peak could also be attributable to any carbonates present in the mineral formation within the oil shale. The carbonate content in any mineral present could, therefore, occult the absorption due to the C=O present in the kerogen.

The carbon-carbon double bond (C=C) absorption region and aromatic carbon-carbon bond absorption region were also determined to be undesirable for determining kerogen content within a sample of oil shale. The C=C and aromatic bond absorption region appears at about 1600 to about 1680 cm$^{-1}$. The oil shale from the Piceance Creek Basin in Colorado and Utah has a relatively low aromatic content. The carbon-carbon aromatic bond does not present a characteristic infrared absorption for such shale oil. Further, the band at which the C=C and aromatic carbon-carbon bond absorption appears within the infrared region is rather noisy and broad. The absorption due to the C=C bonds present in kerogen can be partially occulted by N—O bonds which occur at about the same band. The N—O bonds can be a part of some minerals that can be present in the oil shale.

The portion of the infrared region having a wavelength from about 7 to about 10 microns is undesirable in determining kerogen content. Such a region has many absorbance peaks which are attributable to both kerogen and the minerals present in oil shale. Therefore, such portion provides a poor quantitative measurement for kerogen in the oil shale. Absorption peaks within the portion of the infrared region having wavelengths greater than 10 microns were also found to be less desirable for use in determining kerogen content. Careful sample preparation is needed to minimize variations in the absorption peaks within this region.

The kerogen within the oil shale is the source of organic carbon and substantially all of the carbon-hydrogen bonding which is exhibited in the infrared spectrographic analysis of oil shale. Experimental evidence has shown that concentration of alkyl carbon and hydrogen correlates well with Fischer assay analysis of many types of oil shale. The presence of the C—H bond is an indication of those bonds which are most likely to produce useful shale oil. It follows, therefore, that C—H bond absorbance is the best direct measure of potential Fischer assay oil yield of oil shale.

In the method of this invention a small sample size can be utilized. A sample of 0.1 g can be used to determine kerogen content by this method. Thus, the source of the oil shale to be examined by this method can be very specific, such as a narrow stratum within a large deposit. Such a small sample size necessitates attention to homogeneity of the sample to insure that the material tested is representative of the oil shale formation of interest.

To provide such a homogenous sample a larger sample of the oil shale to be tested is comminuted, such as by grinding and riffling to form a particle size of about $-200$ mesh. These small particles can then be thoroughly mixed to provide the uniform sample of the oil shale. The small particle size also lends itself to infrared analysis. Infrared analysis of solids is conducted by transmitting infrared light through a thin wafer of the substance; such a small particle size is, therefore, useful in creating such a thin wafer for analysis.

In a preferred working embodiment of this method, a sample of oil shale formation is comminuted to a particle size of $-200$ mesh. The powdery-like oil shale is thoroughly intermixed to obtain about a 0.5 g sample which is representative of the oil shale formation. The 0.5 g sample is combined with about 0.5 g of a preformulated 1:1 by weight mixture of KCN and KBr. The preformulated KCN and KBr mixture is previously comminuted to a $-200$ mesh particle size. Using a micro die, a thin transparent wafer of the overall mix is made.

The wafer can be of any desired thickness that provides substantial absorbance to be measurable. In practice, it has been found that a wafer is generally from about 1 to about 10 mm thick. The lower end of the range is selected due to the fragility of a wafer of less than 1 mm in thickness. Shorter pathlengths can be used (i.e. less thickness) if the concentration provides sufficient absorbance of the infrared light as to be measurable. Thicker wafers than 10 mm can also be used but practically generally limits the thickness of 10 mm. When a wider wafer is used, a longer pathlength is provided which allows for less concentration of absorbing material in the sample.

The wafer is placed into an infrared spectrophotometer and an infrared scan is conducted by transmitting infrared light through the wafer. A spectrogram is produced showing the relative absorbance of the kerogen in the sample at the C—H characteristic peak at about 2900 cm$^{-1}$ and the KCN-KBr peak at about 2090 cm$^{-1}$. Rather than conducting an infrared scan of the sample, the sample can be irradiated with the selected light, i.e., with infrared light of 2900 cm$^{-1}$ and the infrared light of 2090 cm$^{-1}$. The absorption peak at about 2090 cm$^{-1}$ for the KCN-KBr mixture is within a portion of the infrared region in which oil shale does not absorb.

Conducting the above described analysis on samples of oil shale having a known kerogen content provides the necessary data for determining the constant, or generating a graph, which can be used to determine unknown concentrations of kerogen. The kerogen concentration in the unknown samples can be determined by measuring the ratio of the infrared absorbances at 2900 cm$^{-1}$ and 2090 cm$^{-1}$ respectively and using the graph or solving the equation (5) using the determined constant.

Utilizing the method of this invention, the yield of shale oil from oil shale can be derived directly and easily from infrared analysis of a sample of the oil shale since the Fischer Assay of kerogen content is an indication of the amount of shale oil recoverable from a quantity of oil shale. The graph of the drawing illustrates a straight-line curve useful in determining the kerogen content of an oil shale sample. An infrared analysis was made of four samples of oil shale having known kerogen contents of 0, 10, 27 and 37 gallons per ton of oil shale. The kerogen content was determined by Fischer assay analysis.

Each of the oil shales of differing kerogen content was separately comminuted to a particle size of about −200 mesh. A 0.5 g sample of each of the −200 mesh oil shales was thoroughly mixed with 0.5 g of a 1:1 by weight mixture of KCN and KBr also comminuted to a particle size of about −200 mesh. A 0.5 g representative sample of each of the oil shales was removed from the mixture and a thin wafer having a thickness of about 3 mm was made using a micro die for each of the samples of oil shale of varying kerogen content.

Each wafer was placed in an infrared spectrophotometer and the infrared absorbance spectrum was obtained. The ratio of the respective absorbances at 2900 cm$^{-1}$ and 2090 cm$^{-1}$ of each wafer was determined and plotted on the graph versus the known kerogen content for each sample. A straight-line curve having a slope of about 110 gallons of shale oil per ton of oil shale was drawn through the locus of points.

The kerogen content, which is equivalent to the Fischer Assay kerogen content or recoverable shale oil content, of a sample of oil shale having an unknown kerogen content is then determined. A thin wafer is prepared from a comminuted sample of the oil shale and the previously prepared KCN and KBr mixture. The ratio of the infrared absorbances for such a wafer at 2900 cm$^{-1}$ and 2090 cm$^{-1}$ is then determined. The absorbances for the kerogen and KCN-KBr mixture can be measured by any convenient method such as by commercially available infrared spectrophotometers. Only the two bands of infrared light, one at 2090 cm$^{-1}$ and one at 2900 cm$^{-1}$, need be transmitted through the sample of oil shale as the absorption peaks for only the kerogen and internal standard are needed to determine the concentration of kerogen at a standardized background. However, as many commercial infrared spectrophotometers are available that scan the entire infrared region of the electromagnetic spectrum in a relatively short time period, such instruments can be used to produce an infrared spectrogram for the sample. If an entire infrared spectrogram is produced, attention to only the respective characteristic absorbances at 2090 cm$^{-1}$ and 2900 cm$^{-1}$ is needed. An advantage of having the entire infrared spectrogram for an oil shale sample is that a total infrared analysis may be useful at some later point in time. After the ratio of the absorbances has been determined, it is multiplied by the slope of the curve, or the constant, to obtain the kerogen content in gallons of shale oil per ton of oil shale.

The method of this invention does, therefore, allow for quick estimation of the shale oil yield from organic rich solids such as oil shale by an infrared absorption analysis. The equipment can be portable for allowing such infrared measurements to be made on or at the site of such oil shale formation. Sample size is small and no chemical degradation of the sample is required. The sample can be retained as the wafer and the comminuted sample of oil shale not used in preparing such a wafer can also be saved for subsequent testing.

What is claimed is:

1. A method for determining the kerogen content of oil shale comprising:
   comminuting oil shale;
   transmitting infrared light from the region of the electromagnetic spectrum having a wave number of from about 4000 to about 625 cm$^{-1}$ through a sample comprising such comminuted oil shale and an internal standard, the internal standard having a known infrared absorbance in a portion of the infrared region of the spectrum in which oil shale does not absorb;
   measuring the absorbance of such infrared light by the sample; and
   correlating the ratio of the absorbance of such infrared light at a first selected wave number in a portion of the infrared region in which oil shale does absorb to the absorbance of such infrared light at a second selected wave number in a portion of the infrared region in which the internal standard absorbs to the kerogen content of such oil shale.

2. A method as recited in claim 1 wherein the first selected wave number is within the carbon-hydrogen bond stretching frequency of the infrared region.

3. A method as recited in claim 2 wherein the first selected wave number is about 2900 cm$^{-1}$.

4. A method as recited in claim 1 wherein the oil shale is comminuted to a powder having a maximum particle size of about −200 mesh.

5. A method as recited in claim 1 wherein the internal standard is selected from the group consisting of KCN, KBr, KSCN and mixtures thereof, with the provision that KBr is not used alone.

6. A method for determining the kerogen content of oil shale comprising:
   comminuting the oil shale to form a representative sample of the oil shale;
   mixing the comminuted oil shale sample with an internal standard having a known infrared absorbance in a portion of the infrared region of the electromagnetic spectrum in which oil shale does not absorb;
   transmitting infrared light from the region of the electromagnetic spectrum having a wave number of from about 4000 to about 625 cm$^{-1}$ through the mixture of comminuted oil shale sample and internal standard;
   measuring the absorbance of such infrared light by the mixture of comminuted oil shale and internal standard over such a region of the electromagnetic spectrum; and
   correlating the ratio of the absorbance of infrared light at a characteristic wave number for kerogen and the absorbance of infrared light at a characteristic wave number for the internal standard to the kerogen content of the sample.

7. A method as recited in claim 6 wherein absorbance is measured at a characteristic wave number for kerogen corresponding to the carbon-hydrogen bond stretching portion of the infrared region.

8. A method as recited in claim 7 wherein the absorbance of infrared light for kerogen is measured at about 2900 cm$^{-1}$.

9. A method as recited in claim 6 wherein the internal standard is a compound or mixture of compounds selected from the group consisting of KCN, KBr and KSCN, with the proviso that KBr is not used alone.

10. A method as recited in claim 6 wherein the internal standard is a 1:1 mixture by weight of KCN and KBr and the absorbance of such an internal standard is measured at about 2090 cm$^{-1}$.

11. A method as recited in claim 6 wherein the oil shale is comminuted for forming a sample having maximum particle size of about −200 mesh.

12. A method for determining shale oil yield by the infrared analysis of oil shale comprising the steps of:
   (a) comminuting an oil shale sample having a known shale oil yield;
   (b) mixing the comminuted oil shale with a comminuted internal standard having a known infrared absorbance in a portion of the infrared region of the electromagnetic spectrum in which kerogen present in oil shale does not absorb;
   (c) transmitting infrared light from the region of the electromagnetic spectrum having a wave number of from about 4000 to about 625 cm$^{-1}$ through the mixture of comminuted oil shale and internal standard;
   (d) measuring the absorbance of infrared light at a characteristic wave number for kerogen present in oil shale and at a characteristic wave number for the internal standard;
   (e) repeating at least once the steps (a) through (d) using an oil shale sample having a known but different shale oil yield;
   (f) generating a straight-line curve by plotting the known shale oil yield for each oil shale sample versus a ratio of the measured absorbances at the characteristic wave number for kerogen and the characteristic wave number for the internal standard for each oil shale sample;
   (g) repeating the steps of (a) through (d) using an oil shale sample having an unknown shale oil yield; and
   (h) correlating the ratio of the measured absorbances at the characteristic wave number for kerogen and the characteristic wave number for the internal standard to the generated straight-line curve for determining the shale oil yield for the unknown oil shale.

13. A method as recited in claim 12 wherein the internal standard is selected from the group consisting of KCN, KBr, KSCN and mixtures thereof, with the proviso the KBr is not used alone.

14. A method as recited in claim 12 wherein the characteristic wave number for kerogen is the portion of the infrared region corresponding to the carbon-hydrogen bond stretching frequency.

15. A method as recited in claim 14 wherein the characteristic wave number for kerogen is about 2900 cm$^{-1}$.

16. A method as recited in claim 12 wherein the internal standard is a 1:1 mixture by weight of KCN and KBr and the absorbance of such an internal standard is measured at about 2090 cm$^{-1}$.

* * * * *